(12) United States Patent
Zhang et al.

(10) Patent No.: US 11,564,558 B2
(45) Date of Patent: Jan. 31, 2023

(54) ADJUSTABLE ENDOSCOPE FIXING DEVICE

(71) Applicant: Shenyang Shengshi Medical Technology Co., LTD., Shenyang (CN)

(72) Inventors: Lijun Zhang, Shenyang (CN); Tao Zhu, Shenyang (CN); Wei Gao, Shenyang (CN)

(73) Assignee: Shenyang Shengshi Medical Technology Co., Ltd., Shenyang (CN)

( * ) Notice: Subject to any disclaimer, the term of this patent is extended or adjusted under 35 U.S.C. 154(b) by 649 days.

(21) Appl. No.: 16/346,992

(22) PCT Filed: Jun. 5, 2017

(86) PCT No.: PCT/CN2017/087204
§ 371 (c)(1),
(2) Date: May 2, 2019

(87) PCT Pub. No.: WO2018/082303
PCT Pub. Date: May 11, 2018

(65) Prior Publication Data
US 2019/0254507 A1 Aug. 22, 2019

(30) Foreign Application Priority Data
Nov. 2, 2016 (CN) .......................... 201621176474.2

(51) Int. Cl.
*A61B 1/00* (2006.01)
*A61B 1/307* (2006.01)

(52) U.S. Cl.
CPC ...... *A61B 1/00142* (2013.01); *A61B 1/00066* (2013.01); *A61B 1/00112* (2013.01);
(Continued)

(58) Field of Classification Search
CPC ............ A61B 1/00105; A61B 1/00121; A61B 1/00131; A61B 1/00135; A61B 1/00142;
(Continued)

(56) References Cited

U.S. PATENT DOCUMENTS

| 4,258,721 A | * | 3/1981 | Parent ................. A61B 1/00108 604/26 |
| 4,374,523 A | * | 2/1983 | Yoon ....................... A61F 6/208 606/140 |
| 4,718,419 A | | 1/1988 | Okada |

(Continued)

FOREIGN PATENT DOCUMENTS

| CN | 106361388 A | 2/2017 |
| CN | 106618448 A | 5/2017 |

(Continued)

OTHER PUBLICATIONS

International Patent Application No. PCT/CN2017/087204; Int'l Written Opinion and Search Report; dated Aug. 25, 2017; 12 pages.

*Primary Examiner* — Ryan N Henderson
(74) *Attorney, Agent, or Firm* — Caesar Rivise, PC (57) ABSTRACT

An adjustable endoscope fixing device, comprises a tail bed, a three-way connector and a locking screw; an outer wall surface of a straight column section of the tail bed is provided with a rectangular slot; and an outer wall surface of a first connecting end of the three-way connector is provided with a locking structure, and the straight column section of the tail bed is connected to the first connecting end of the three-way connector, and the tail bed is fixed to the three-way connector by the locking structure.

8 Claims, 6 Drawing Sheets

(52) U.S. Cl.
CPC ...... *A61B 1/00135* (2013.01); *A61B 1/00147* (2013.01); *A61B 1/307* (2013.01)

(58) Field of Classification Search
CPC ............ A61B 1/00147; A61B 1/00154; A61B 1/00195; A61B 1/303; A61B 1/307; A61B 1/313; A61B 17/3421; A61B 1/00112
See application file for complete search history.

(56) References Cited

U.S. PATENT DOCUMENTS

| | | | | |
|---|---|---|---|---|
| 5,169,397 | A * | 12/1992 | Sakashita | A61B 18/149 606/205 |
| 5,312,418 | A * | 5/1994 | Bonnet | A61B 17/22 606/1 |
| 5,685,853 | A * | 11/1997 | Bonnet | A61B 17/3478 600/156 |
| 6,106,494 | A * | 8/2000 | Saravia | A61M 3/0216 604/35 |
| 8,852,085 | B2 * | 10/2014 | Shener-Irmakoglu | A61B 1/00068 600/105 |
| 2003/0009175 | A1 * | 1/2003 | Cassidy, Jr. | A61B 17/3421 606/108 |
| 2006/0293560 | A1 * | 12/2006 | Nguyen | A61F 6/06 600/104 |
| 2009/0221873 | A1 * | 9/2009 | McGrath | A61B 1/00128 600/153 |
| 2012/0197119 | A1 | 8/2012 | Takachi | |
| 2014/0005478 | A1 * | 1/2014 | Kennedy, II | A61B 10/04 600/114 |
| 2015/0025315 | A1 * | 1/2015 | Nishina | A61B 10/0275 600/104 |
| 2017/0007103 | A1 * | 1/2017 | Hashiguchi | A61B 1/018 |

FOREIGN PATENT DOCUMENTS

| | | |
|---|---|---|
| EP | 0745347 A2 | 12/1996 |
| EP | 1859747 A1 | 11/2007 |

* cited by examiner

ADJUSTABLE ENDOSCOPE FIXING DEVICE

CROSS-REFERENCE TO RELATED APPLICATIONS

This application is the National Stage of International Application No. PCT/CN2017/087204, filed on Jun. 5, 2017, which claims priority to Chinese Patent Application No. 201621176474.2, filed on Nov. 2, 2016, both of which are hereby incorporated by reference in their entireties.

TECHNICAL FIELD

The present application relates to an endoscope sheath, and particularly relates to an endoscope fixing device with adjustable endoscope positions.

BACKGROUND ART

The endoscopes used for the surgeries on urinary system and bladder are generally defined as precise instrument, and have high prices and high costs for maintenance and cleaning, and too frequent cleaning shortens the service life of the instrument. The actual surgeries always employ a disposable endoscope sheath to insert into a human body, to not contact the endoscope directly with the human body, to avoid the endoscope from being contaminated by bacteria. After the surgery has ended, the disposable endoscope sheath can be discarded, and the endoscope is merely required to be simply rinsed.

Conventional endoscope tail beds and the sheath main body are usually of an integral structure, and the tail bed cannot be detached from the sheath main body, which results in the inconvenience in the installation of the endoscope. Additionally, the position of the endoscope cannot be adjusted in the process of a surgery, and the operation is inconvenient, which makes the surgery difficult to a certain extent.

SUMMARY OF THE DISCLOSURE

An object of the present application is to provide an adjustable endoscope fixing device, to solve the problem of the conventional endoscope sheath fixing devices that the position cannot be adjusted and the operation is inconvenient.

In order to achieve the above object, the present application discloses an adjustable endoscope fixing device, wherein the adjustable endoscope fixing device comprises a tail bed, a three-way connector and a locking screw;

an outer wall surface of a straight column section of the tail bed is provided with a rectangular slot; an outer wall surface of a first connecting end of the three-way connector is provided with a locking structure, and the straight column section of the tail bed is connected to the first connecting end of the three-way connector, and the tail bed is fixed to the three-way connector by the locking structure.

Optionally, the outer wall surface of the first connecting end of the three-way connector is provided with a threaded through hole; and the locking structure is formed by the locking screw passing through the threaded through hole of the three-way connector, and being screwed into the rectangular slot of the tail bed, to fix the tail bed to the three-way connector.

Optionally, the outer wall surface of the first connecting end of the three-way connector is provided with a tab, and the tab is provided with a threaded through hole in a center.

Optionally, an outer wall surface of the tail bed is provided with a key-shaped protrusion; and an inner hole of the first connecting end of the three-way connector is provided with a key slot.

Optionally, the straight column section provided with the key-shaped protrusion of the outer wall surface of the tail bed is inserted into the inner hole provided with the key slot of the first connecting end of the three-way connector.

Optionally, the tail bed is of a funnel shape having a central hole, the tail bed comprises a top portion and a neck portion, the neck portion is a straight column section whose outer wall is provided with a step, the outer wall surface is provided with a key-shaped protrusion, and the protrusion is provided with a rectangular slot.

Optionally, the first connecting end of the three-way connector is a straight column section whose interior has a two-section stepped hole and whose outer wall surface has a square tab, and a first section of the stepped hole is an inner hole having a key slot; and the square tab of the three-way connector is located on the outer wall corresponding to the key slot, the square tab is provided with a threaded through hole in a center, and the through hole extends to an inner surface of the key slot.

Optionally, the key-shaped protrusion of the tail bed and the key slot of the three-way connector are in clearance fit.

Optionally, the rectangular slot of the tail bed is of an elongated shape, and the locking screw is able to be fixed to any position of the rectangular slot.

Particularly, an endoscope sheath is provided, wherein the endoscope sheath comprises the fixing device, a lock buckle, a four-way connector, a valve, a probe tube, a probe head, a thick pipe, a thin pipe and a lock buckle cap;

the fixing device comprises the tail bed, the three-way connector and the locking screw;

the lock buckle is mounted on the tail bed, the tail bed is connected to the first connecting end of the three-way connector, a second connecting end of the three-way connector is an instrument entrance, a third connecting end of the three-way connector is connected to a connecting end of the four-way connector, one end of the probe tube is connected to another connecting end of the four-way connector, and the probe head is connected to the other end of the probe tube.

In the device of the present application, by connecting the key and the key slot and fixing by using the locking screw, the tail bed connected to the endoscope can be conveniently detached, and, by varying the position of the locking screw in the rectangular slot, the position of the tail bed can be varied, to facilitate finely tuning the position of the endoscope in practice operation processes.

The other characteristics and advantages of the present application will be described in the subsequent description, and partially become apparent from the description or be understood by the implementation of the present application. The objects and the other advantages of the present application can be implemented and obtained from the structures particularly illustrated in the written description, claims and drawings.

BRIEF DESCRIPTION OF DRAWINGS

The drawings are merely for the purpose of illustrating the particular embodiments, and are not considered as limitation to the present application. Throughout the drawings, the same reference signs denote the same elements.

The reference numbers in the drawings: 11—lock buckle, 12—tail bed, 13—three-way connector, 14—four-way connector, 15—locking screw, 16—valve, 17—probe tube, 18—probe head, 19—thick pipe, 20—thin pipe, 21—lock buckle cap; 131—first connecting end, 132—second connecting end, 133—third connecting end; and 22—rectangular slot.

DETAILED DESCRIPTION

The preferable embodiments of the present application will be particularly described below with reference to the drawings. The drawings form a portion of the present application, and are for explaining the principle of the present application together with the embodiments of the present application.

Figure 1:
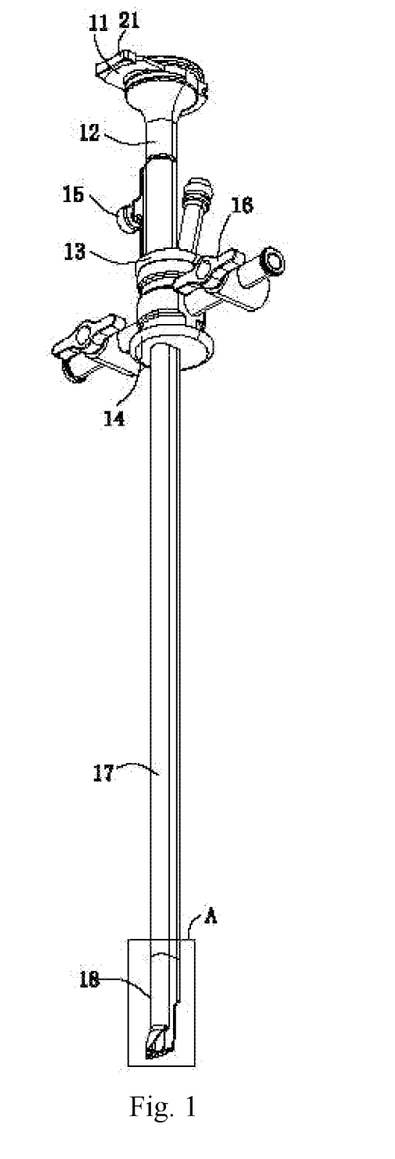
FIG. 1 is a schematic diagram of the overall structure of the present application.
Figure 2:
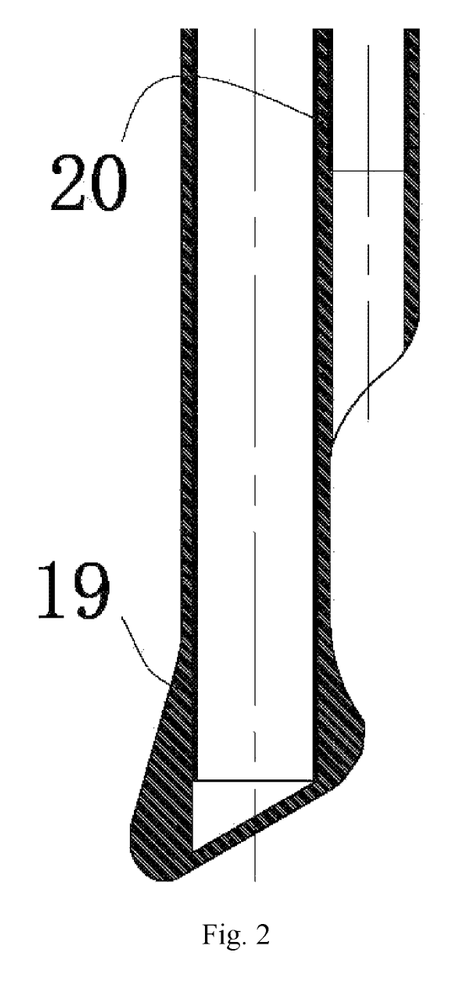
FIG. 2 is a partial enlarged view of the A in the overall structure of the present application.

The present application discloses an automatic endoscope locking device. As shown in FIG. 1, the automatic endoscope locking device comprises: a lock buckle 11, a tail bed 12, a three-way connector 13, a four-way connector 14, a locking screw 15, a valve 16, a probe tube 17, a probe head 18, a thick pipe 19, a thin pipe 20 and a lock buckle cap 21.

The lock buckle 11 is mounted on the tail bed 12, the tail bed 12 is connected to a first connecting end 131 of the three-way connector 13, a second connecting end 132 of the three-way connector 13 is an instrument entrance, a third connecting end 133 of the three-way connector 13 is connected to a connecting end of the four-way connector 14, one end of the probe tube 17 is connected to another connecting end of the four-way connector 14, and the probe head 18 is connected to the other end of the probe tube 17.

The locking device is of a snap ring type, and the lock buckle 11 is elastically connected to the tail bed 12 via an elastic rubber ring.

Figure 3:
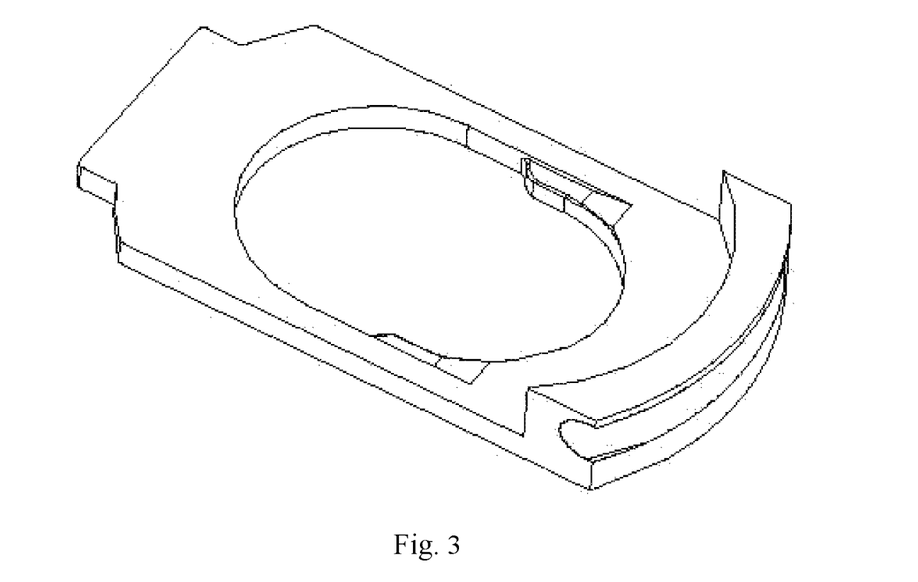
FIG. 3 is a structural diagram of the lock buckle of the present application.

As shown in FIG. 3, the lock buckle 11 is of a cuboidal sheet structure. One end of the lock buckle 11 is a step having a circular arc transition, and a lock buckle cap 21 is mounted on the step, for pressing the lock buckle, to facilitate the operation. The other end of the lock buckle 11 is a circular arc, and the lock buckle 11 is provided with an oblong hole in the center, which is the central hole. The circular arc end of the lock buckle 11 is provided with a protrusion, the protrusion is provided with a groove for mounting the elastic rubber ring, the protrusion is of a circular arc shape, and the circular arc shape matches with the shape of the position of the tail bed 12 where the lock buckle 11 is mounted, to facilitate the lock buckle 11 mounting on the tail bed 12. The radius of the end of the central hole adjacent to the circular arc end of the lock buckle 11 is equal to the radius of the endoscope, whereby the endoscope can be fastened without scratching the surface of the endoscope, and the radius of the other end of the central hole is greater than the radius of the endoscope, to facilitate the mounting.

Figure 4:
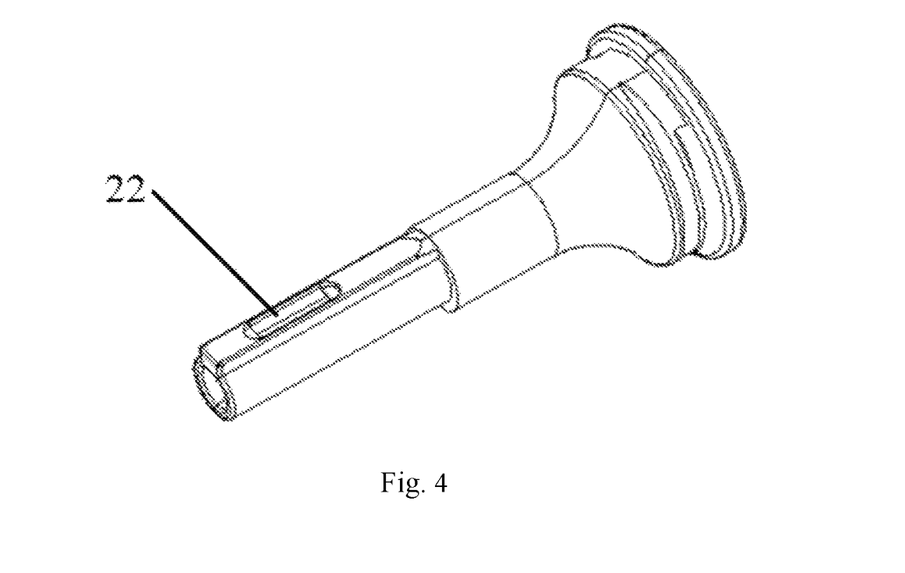
FIG. 4 is a structural diagram of the tail bed of the present application.

As shown in FIG. 4, the tail bed 12 is of a funnel shape having a central hole, the tail bed 12 comprises a top portion and a neck portion, and the top portion of the tail bed 12 is provided with a slot for mounting the lock buckle 11 and a groove for mounting the elastic rubber ring. The two sides of the slot are closed, to prevent the mismatching of the central hole of the lock buckle 11 and the hole within the tail bed 12, and the two ends of the slot are open, to enable the lock buckle 11 to move reciprocately within the slot along the oblong hole. The top portion of the central hole of the tail bed 12 is a connector for mounting the endoscope, the connector is provided with a hole therewithin, and a diameter of the hole is greater than a diameter of the endoscope, to facilitate the mounting.

The lock buckle 11 is mounted within the slot of the tail bed 12 via the central hole of the lock buckle 11, and is movable reciprocately. The elastic rubber ring is mounted in the groove of the lock buckle 11 and the groove of the tail bed 12, so that the lock buckle 11 and the tail bed 12 are elastically connected. In the normal state, because the elastic rubber ring has elasticity, the step end of the lock buckle 11 is deviated from the central hole of the tail bed 12, the end that has the equal radius with the endoscope of the central hole of the lock buckle 11 coincides with the connector of the tail bed 12, the other end of the central hole of the lock buckle 11 is blocked by the tip of the tail bed 12. When the step end of the lock buckle 11 is being pressed, the end of the central hole of the lock buckle 11 that is greater than the radius of the endoscope coincides with the connector of the tail bed 12, and the other end of the central hole of the lock buckle 11 is blocked by the tip of the tail bed 12, at which time the endoscope can be installed.

When the endoscope is being installed, the step end of the lock buckle 11 is pressed, and the central hole on the lock buckle 11 that has the radius equal to that of the connector of the tail bed 12 coincides with the hole of the connector end of the tail bed 12, the endoscope is inserted into the lock buckle 11 and the tail bed 12, the step end of the lock buckle 11 is released, and because the elastic rubber ring has elasticity, the lock buckle 11 is repositioned, and the oblong hole of the lock buckle 11 with the radius equal to that of the endoscope clips the endoscope, and the endoscope is fixed.

The tail bed 12 is fixedly connected to one end of the three-way connector 13 by a key slot and the locking screw 15.

Figure 5:
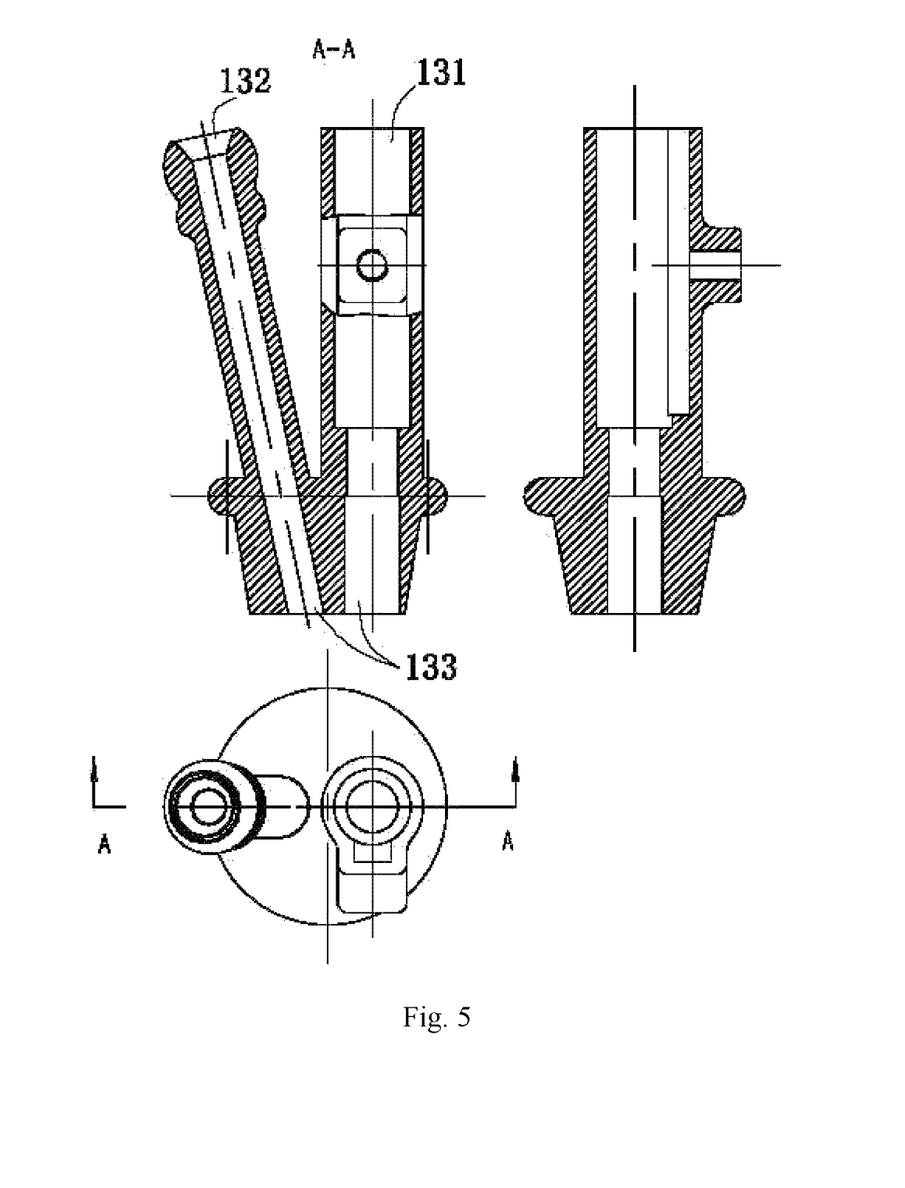
FIG. 5 is a structural diagram of the three-way connector of the present application.

As shown in FIG. 4, the neck portion of the tail bed 12 is a straight column section whose outer wall has a step, which can be very easily inserted into a through hole of the three-way connector 13. The outer wall surface of the straight column section is provided with a key-shaped protrusion, and the protrusion is provided with a rectangular slot 22, wherein the rectangular slot 22 is for mounting the locking screw. As shown in FIG. 5, the three-way connector 13 is provided with three port ends, wherein the first connecting end 131 is connected to the tail bed 12. The first connecting end 131 is a straight column section whose interior has a two-section stepped hole and whose outer wall surface has a square tab. The first section of the stepped hole is an inner hole having a key slot, and the key slot is matched with the key-shaped protrusion of the tail bed. The inner diameter of the second section of the stepped hole is less than the inner diameter of the first section. The square tab is located on the outer wall corresponding to the key slot, the square tab is provided with a threaded through hole in the center, and the threaded through hole extends to the inner surface of the key slot, for mounting the locking screw.

The straight column section of the tail bed 12 is inserted into the first section of the stepped hole of the three-way connector 13, and the key slot is in clearance fit to the key-shaped protrusion, which facilitates the dismounting. The locking screw 15 passes through the threaded through hole of the tab of the three-way connector 13, and is screwed into the rectangular slot of the tail bed 12 tightly, whereby the tail bed 12 is fixed on the three-way connector 13. The rectangular slot of the tail bed 12 is of an elongated shape, and the locking screw 15 may be fixed at any position of the rectangular slot. When the position of the tail bed 12 is required to be changed, the locking screw 15 is unscrewed, the tail bed 12 is moved to the required position, and the locking screw 15 is screwed tightly again. In this way, although the dimensions of the tail bed 12 and the three-way connector 13 are not greatly changed, the position of the locking screw 15 in the rectangular slot can be varied according to the demands, to in turn vary the position of the tail bed 12. Such a variation of a small amplitude can hugely facilitate the practice operations.

In this embodiment, preferably, the dimensions of the rectangular slot of the tail bed 12 are 7.5×2.25×0.98 mm, and the specification of the locking screw is M2.5.

As shown in FIG. 5, the second connecting end 132 of the three-way connector 13 is inclined by 12°, for the inserting of instruments such as surgical scissors. The third connecting end 133 of the three-way connector 13 directly communicates with the first connecting end 131, and the third connecting end 133 has a diameter greater than that of the second stepped section of the first connecting end 131. The third connecting end 133 of the three-way connector 13 is connected to the top of the four-way connector 14, the left and right ends of the four-way connector 14 are respectively connected to a water inlet pipe and a water outlet pipe, the water in the water inlet pipe enters a human body via the left end of the four-way connector 14, the contaminated water in the human body is discharged via the right end of the four-way connector 14, and the left and right ends of the four-way connector 14 are provided with through holes for mounting the valve 16, to control the connecting and breaking of the pipeline. The bottom end of the four-way connector 14 is connected to one end of the probe tube 17, and the other end of the probe tube 17 is connected to the probe head 18.

Figure 6:
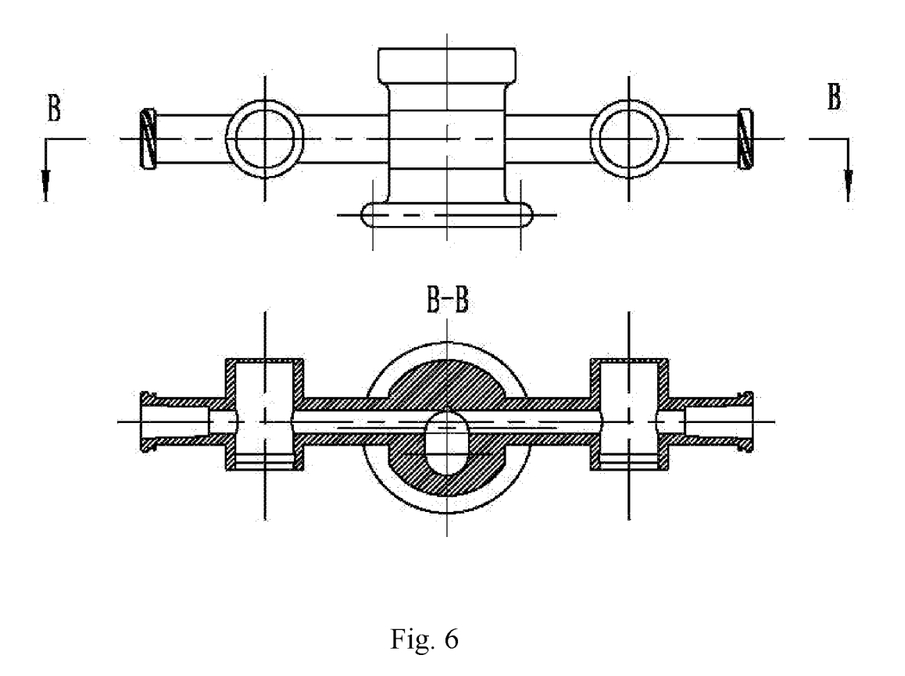
FIG. 6 is a structural diagram of the four-way connector of the present application.

As shown in FIG. 6, an oblong through hole is between the upper and lower ends of the four-way connector 14, and both of the left and right ends of the four-way connector 14 are provided with through holes, which communicate with one end of the oblong hole.

Figure 7:
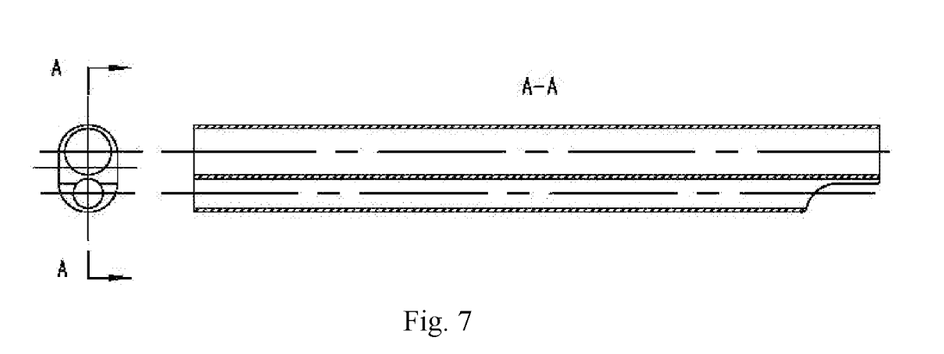
FIG. 7 is a schematic diagram of the mounting of the probe tube and the probe head of the present application.

As shown in FIG. 7, the probe tube 17 is a long-cylinder-shaped straight tube, with a cross-section of an oblong shape, and comprises two straight through round holes, one with a larger diameter and the other one with a smaller diameter, and the two straight through round holes do not communicate.

Figure 8:
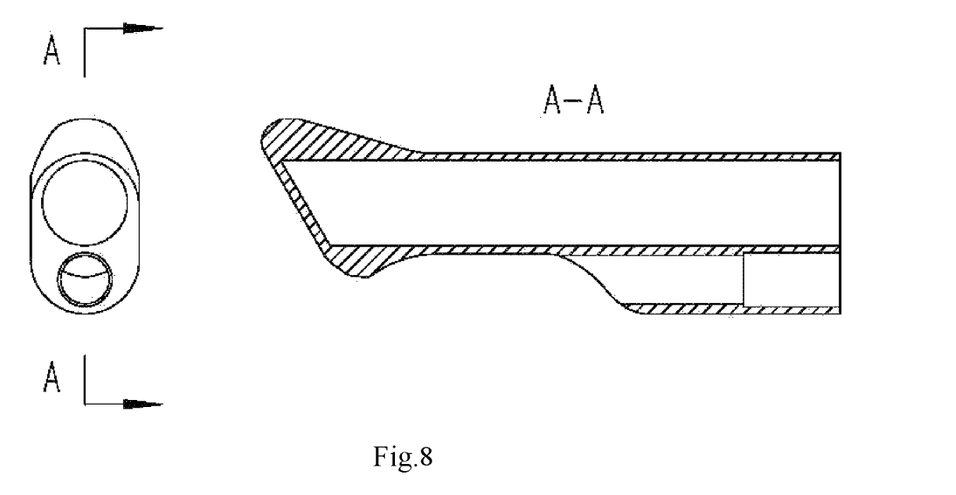
FIG. 8 is a structural diagram of the probe head of the present application.

The probe head 18 is a long-cylinder-shaped straight tube, and comprises two straight through round holes, one with a larger diameter and the other one with a smaller diameter. The front end of the straight through round hole with the larger diameter is inclined by 60°, and the inclining position is provided with a transparent viewing window. The round hole with the larger diameter is closed by the transparent viewing window, and the transparent viewing window facilitates the observation with the endoscope. The tip of the straight through round hole with the larger diameter is a round tip with a circular arc transition, whereby the sheath can be conveniently inserted into a human body, and not cause scratching. The length of the round hole with the smaller diameter is shorter than the length of the round hole with the larger diameter, and the tip of the straight through round hole with the smaller diameter is inclined by 60°.

The thick pipe 19 is mounted within the round tube with the larger diameter of the probe tube 17, and the thin pipe 20 is mounted within the round tube with the smaller diameter. One end of the thick pipe 19 is inserted into the round tube with the larger diameter of the probe head 18 via the probe tube 17, and is fixedly connected to the probe head, and the other end of the thick pipe 19 is inserted into the first section of the stepped hole of the first connecting end 131 of the three-way connector 13 via an oblong through hole of the four-way connector 14. The inner diameter of the second section of the stepped hole of the first connecting end 131 is less than the external diameter of the thick pipe 19, so that the thick pipe 19 and the first connecting end 131 are connection of interference fit, whereby the probe head 18 is fixed to the probe tube 17 via the thick pipe 19. The thin pipe 20 is mounted within one end of the oblong hole of the four-way connector 14, and the end of the oblong hole is adjacent to the left and right through holes, the thin pipe 20 communicate with the left and right through holes, and the thick pipe 19 is mounted at the other end of the oblong hole. The thin pipe 20 is mounted within the round hole with the smaller diameter of the probe tube, wherein one end is fixed to the oblong through hole of the four-way connector 14, and communicates with the through holes of the left and right ends of the four-way connector 14, and the other end is inserted into the probe head 18.

One end of the thick pipe 19 is fixed within the round hole with the larger diameter of the probe head 18. The probe tube 17, the four-way connector 14 and the thick pipe 19 are in clearance fit, to enable the thick pipe 19 to be very easily drawn from the round hole. The thick pipe 19 is in interference fit to the first connecting end 131 of the three-way connector 13, whereby the thick pipe 19 does not fall freely during usage. The outer surface of the thick pipe 19 is printed with a plurality of strip-shaped metal round rings, to increase the friction between the thick pipe 19 and the inner wall of the probe tube 17, and prevent the thick pipe 19 from falling in the process of drawing the thick pipe 19

Endoscope sheaths are generally formed by extrusion integrally. The manufacturing process cannot ensure the finish degree of the inner surface of the probe tube 17, and if the inner surface is further processed, the cost of the process is too high. Moreover, both of the thick pipe 19 and the thin pipe 20 are made from stainless steel, which can ensure the straightness and smoothness of the inner wall, and has the advantages of a high strength and a high rigidity. When the thick pipe 19 and the thin pipe 20 are mounted within the probe tube, the rigidity and strength of the probe tube can be significantly increased, and the probe tube does not easily bend and transform in the process of the insertion into a human body and does not easily fall in the process of a surgery.

On the basis of the above structures, the second connecting end 132 of the three-way connector 13, the four-way connector 14, the thin pipe 20 within the round hole with the smaller diameter of the probe tube 17 and the probe head 18 form an instrument channel, for delivering the instrument into a human body in the process of a surgery for operation, and the lock buckle 11, the tail bed 12, the first connecting end 131 of the three-way connector 13 and the thick pipe 19 form an endoscope channel, for delivering the endoscope to the site to be observed.

Because the probe head 18 is provided with the transparent viewing window at the tip, the endoscope does not contact with the human body or any liquid, which ensures the cleanness of the endoscope. By using the valve 16 on the four-way connector 14, external water can enter the human body via the instrument channel, and then the contaminated water can be discharged via the instrument channel through the valve 16.

In usage, firstly the sheath is inserted into the human body, a water inlet pipeline and a water outlet pipeline are respectively connected to the left and right ends of the four-way connector 14, the valve 16 connected to the water outlet pipeline is shut, the valve 16 connected to the water inlet pipeline is opened, the water enters the human body via the instrument channel, then the valve 16 connected to the water inlet pipeline is shut, the valve 16 connected to the water outlet pipeline is opened, and the contaminated water is discharged. The lock buckle cap 21 on the lock buckle 11 is pressed, to coincide the central hole on the lock buckle 11 that has the radius equal to that of the connector of the tail bed 12 and the hole of the connector end of the tail bed 12, the tip of the endoscope is inserted into the thick pipe 19, the transparent viewing window is used for observation, the step end of the lock buckle 11 is released, the lock buckle 11 is repositioned by the elasticity of the elastic rubber ring, and the end of the oblong hole with the radius equal to that of the endoscope clips the endoscope, and the endoscope is fixed. The instrument such as medical scissors enters the four-way connector 14 and the thin pipe 20 via the second connecting end 132 of the three-way connector 13, and passes through the probe head 18 into the human body for operation.

After the surgery has ended, the step end of the lock buckle 11 is pressed, to coincide the central hole on the lock buckle 11 that has the radius equal to that of the connector of the tail bed 12 and the hole of the connector end of the tail bed 12, the endoscope is taken out, the instrument is taken out at the same time, and the sheath is taken out of the human body. Because the endoscope did not contact with the human body or other liquids, the endoscope can be used for a next surgery after merely a simple disinfection, which is convenient.

In conclusion, the present application provides an adjustable endoscope fixing device. By connecting the key and the key slot and fixing by using the locking screw, the tail bed connected to the endoscope can be conveniently detached, and, by varying the position of the locking screw in the rectangular slot, the position of the tail bed can be varied, to facilitate finely tuning the position of the endoscope in practice operation processes.

The above are merely preferable particular embodiments of the present application, and the protection scope of the present application is not limited thereto. All of the variations or substitutions that a person skilled in the art can easily envisage within the technical scope disclosed by the present application should fall within the protection scope of the present application.

What is claimed is:

1. An endoscope sheath, comprising: a fixing device, a lock buckle, a four-way connector, a valve, a probe tube, a probe head, a thick pipe, a thin pipe and a lock buckle cap;
    wherein the fixing device comprises a tail bed, a three-way connector and a locking screw; an outer wall surface of a straight column section of the tail bed is provided with a rectangular slot, and the straight column section of the tail bed is connected to the first connecting end of the three-way connector;
    wherein an outer wall surface of a first connecting end of the three-way connector is provided with a threaded through hole; and the locking screw passes through the threaded through hole of the three-way connector, screws into the rectangular slot of the tail bed, to fix the tail bed to the three-way connector;
    wherein the lock buckle is mounted on the tail bed, a second connecting end of the three-way connector is an instrument entrance, a third connecting end of the three-way connector is connected to a connecting end of the four-way connector, one end of the probe tube is connected to another connecting end of the four-way connector, and the probe head is connected to the other end of the probe tube.

2. The endoscope sheath according to claim 1, wherein the outer wall surface of the first connecting end of the three-way connector is provided with a tab, and the tab is provided with the threaded through hole in a center.

3. The endoscope sheath according to claim 2, wherein an outer wall surface of the tail bed is provided with a key-shaped protrusion; and an inner hole of the first connecting end of the three-way connector is provided with a key slot.

4. The endoscope sheath according to claim 3, wherein the straight column section provided with the key-shaped protrusion of the outer wall surface of the tail bed is inserted into the inner hole provided with the key slot of the first connecting end of the three-way connector.

5. The endoscope sheath according to claim 4, wherein the tail bed is of a funnel shape having a central hole, the tail bed comprises a top portion and a neck portion, the neck portion is a straight column section whose outer wall is provided with a step, the outer wall surface is provided with a key-shaped protrusion, and the protrusion is provided with the rectangular slot.

6. The endoscope sheath according to claim 5, wherein the first connecting end of the three-way connector is a straight column section whose interior has a two-section stepped hole and whose outer wall surface has a square tab, and a first section of the stepped hole is an inner hole having a key slot; and the square tab of the three-way connector is located on the outer wall corresponding to the key slot, the square tab is provided with a threaded through hole in a center, and the through hole extends to an inner surface of the key slot.

7. The endoscope sheath according to claim 6, wherein the key-shaped protrusion of the tail bed and the key slot of the three-way connector are in clearance fit.

8. The endoscope sheath according to claim 7, wherein the rectangular slot of the tail bed is of an elongated shape, and the locking screw is able to be fixed to any position of the rectangular slot.

* * * * *